United States Patent
Zhang et al.

(10) Patent No.: US 11,926,587 B2
(45) Date of Patent: Mar. 12, 2024

(54) PROCESS FOR CONVERTING RAFFINATE BUTENES TO PROPYLENE

(71) Applicant: Lyondell Chemical Technology, L.P., Houston, TX (US)

(72) Inventors: Lei Zhang, Houston, TX (US); Pranit S. Metkar, Houston, TX (US); Majid Keyvani, Houston, TX (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 2 days.

(21) Appl. No.: 17/474,953

(22) Filed: Sep. 14, 2021

(65) Prior Publication Data
US 2022/0081376 A1    Mar. 17, 2022

Related U.S. Application Data

(60) Provisional application No. 63/078,661, filed on Sep. 15, 2020.

(51) Int. Cl.
*C07C 6/04* (2006.01)

(52) U.S. Cl.
CPC ..................... *C07C 6/04* (2013.01)

(58) Field of Classification Search
CPC ............ C07C 7/04; C07C 7/005; B01D 3/143
See application file for complete search history.

(56) References Cited

U.S. PATENT DOCUMENTS

| | | | |
|---|---|---|---|
| 6,580,009 B2 | 6/2003 | Schwab et al. | |
| 6,646,172 B1 | 11/2003 | Schwab et al. | |
| 6,777,582 B2 | 8/2004 | Gartside et al. | |
| 8,704,029 B2 | 4/2014 | Nicholas et al. | |
| 8,722,950 B2 | 5/2014 | van Hal et al. | |
| 9,422,209 B2 | 8/2016 | Stanley et al. | |
| 2005/0014981 A1 | 1/2005 | Gartside et al. | |
| 2006/0047176 A1 | 3/2006 | Gartside et al. | |
| 2012/0165590 A1 * | 6/2012 | Liu | C10G 29/205 585/643 |

(Continued)

FOREIGN PATENT DOCUMENTS

| | | | |
|---|---|---|---|
| CA | 2733890 A1 * | 2/2010 | ............... C07C 1/20 |
| EP | 2374780 A1 | 10/2011 | |
| WO | 2010019595 A2 | 2/2010 | |

OTHER PUBLICATIONS

The International Search Report and The Written Opinion for PCT/US2021/050283 dated Jan. 21, 2022.

*Primary Examiner* — Thuan D Dang

(57) ABSTRACT

Disclosed herein is a process for upgrading a raffinate butene (C4 Raffinate) stream to propylene which can produce polymer grade propylene (PGP) by a metathesis process, without consuming fresh ethylene as a feedstock. By recycling ethylene byproduct in the metathesis equilibrium, propylene selectivity can be further improved without negatively impacting butene conversion. Additionally, upon PGP separation, this technology can provide an effluent acceptable for alkylate production by achieving a balanced butene conversion and heavies coproduction. The disclosed process is a relatively low temperature process which can be deployed as a drop-in option for conventional ethylene/butene metathesis unit and provide additional flexibility to existing operations to balance the supply and demand of C2-C4 light olefins.

18 Claims, 4 Drawing Sheets

(56) References Cited

U.S. PATENT DOCUMENTS

2015/0119612 A1* 4/2015 Agrawal ............... B01D 3/141
585/16
2017/0001927 A1 1/2017 Al-Khattaf et al.

* cited by examiner

PROCESS FOR CONVERTING RAFFINATE BUTENES TO PROPYLENE

CROSS REFERENCE TO RELATED APPLICATIONS

This application claims the benefit of priority to U.S. Provisional Application No. 63/078,661, filed on Sep. 15, 2020, which is incorporated herein by reference in its entirety.

TECHNICAL FIELD

This disclosure relates to processes for producing propylene, in particular, butene metathesis processes for producing propylene.

BACKGROUND

Propylene is an important base chemical for a wide variety of applications from plastics to fuels to functional derivatives. Conventionally, propylene is separated as a byproduct from petrochemical refineries. However, increased cracking of shale gas and lighter feeds limits the propylene production, at a time when worldwide propylene demands are growing. Several on-purpose propylene technologies are available, with widely used technologies including propane dehydrogenation (PDH), olefin metathesis, and methanol-to-propylene (MTP). Unfortunately, these technologies have significant shortcomings. For example, PDH requires high capital investment. MTP requires high operation temperatures that lead to unfavorable propylene selectivity and coking of the active sites on the MTP catalysts. Further, on-purpose propylene production via conventional metathesis from ethylene and butenes is attractive only when the propylene/ethylene pricing spread is significant as it consumes valuable ethylene as well. Consequently there is need for new technologies and further options for commercial-scale, on-purpose propylene production.

Compared to MTP and PDH, metathesis approach for propylene production is still appealing for its mild process temperature, therefore less energy intensive. It is further desirable to employ the metathesis process for propylene production from butenes only without consuming fresh valuable ethylene. Therefore, there remains a need for new on-purpose propylene technologies including new metathesis technologies, which may selectively produce larger amounts of propylene to meet global demand and which may avoid some of the costs of ethylene in the process.

SUMMARY OF THE DISCLOSURE

This disclosure provides a process for converting a raffinate butene (C4 Raffinate or C4 Raff) stream to propylene which can produce polymer grade propylene (PGP) from the C4 Raffinate stream by an autometathesis process of butenes, without consuming fresh ethylene. If desired the ethylene byproduct in the metathesis equilibrium may be recycled, and in doing so propylene selectivity can be further improved without negatively impacting butene conversion. Upon PGP separation, the remaining C4+ olefins can be consumed by an alkylation unit (i.e., a unit for converting normal butenes and isobutane into an additive to improve gasoline octane numbers). This low temperature process can be deployed as a drop-in option for a conventional metathesis unit for propylene from the reaction of ethylene and butenes and provide additional flexibility to existing operations to balance the supply and demand of C2-C4 light olefins.

In embodiments, there is provided a process for converting a C4 Raffinate stream to propylene, the process comprising: a) providing a C4 Raffinate stream comprising 1-butene and 2-butene to a metathesis reactor, the metathesis reactor containing a metathesis catalyst system, the metathesis catalyst system including a metathesis catalyst such as those based on Mo and W and optionally including an isomerization catalyst based on K or Mg, and the like; b) contacting the C4 Raffinate stream with the metathesis catalyst system in the absence of ethylene as a feedstock under conditions suitable for forming an intermediate product stream comprising propylene, a heavy (C4+) component, and ethylene; and c) discharging the intermediate product stream to a first separation unit and separating the intermediate product stream into fractions comprising [1] a first product stream having a higher propylene concentration than the intermediate product stream and [2] a second product stream having a lower propylene concentration than the intermediate product stream.

The step of contacting the C4 Raffinate stream with the metathesis catalyst system to form the intermediate product stream is carried out in the absence of freshly-added ethylene, that is, in the absence of ethylene as a feedstock. For example, the C4 Raffinate stream such as Raffinate 1 or Raffinate 2 or Raffinate 3 comprising 1-butene and 2-butene can be provided to the metathesis reactor in the absence of added ethylene to effect the disclosed process.

Following autometathesis of the C4 Raffinate stream, the intermediate product stream can be further separated into product streams in various ways. In embodiments, the first separation unit can be a distillation unit which is adapted to function as a de-ethanizer to separate the intermediate product stream into fractions comprising [1] the first product stream comprising propylene and the heavy (C4+) component as a bottom fraction and [2] the second product stream comprising ethylene as an overhead fraction. If desired, the overhead ethylene fraction can be recycled to the metathesis reactor or C4 Raffinate stream, while the first product stream comprising propylene and the heavy (C4+) component can be send to a de-propanizer column to remove propylene as an overhead fraction and the C4+ component as a bottom fraction.

In other embodiments, the first separation unit can be a first distillation unit which is adapted to function as a de-propanizer to separate the intermediate product stream into fractions comprising [1] the first product stream comprising propylene and ethylene as an overhead fraction and [2] the second product stream comprising the heavy (C4+) component as a bottom fraction. The overhead propylene and ethylene fraction can be send to a downstream de-ethanizer column to remove ethylene as an overhead fraction and remove propylene as a bottom fraction. If desired, the overhead ethylene fraction can be recycled to the metathesis reactor or C4 Raffinate stream. The second product stream comprising the heavy (C4+) component as bottom fraction can be routed to an alkylation unit if desired.

In other embodiments, the intermediate product stream can be separated with a divided wall column where the column overhead comprises ethylene and the column bottom comprises the heavy (C4+) component. The PGP product can be exited from the column around the middle of the column. A divided wall column is a single shell, fully thermally coupled distillation column capable of separating mixtures of three or more components into high purity products. Compared to conventional columns-in-series and/or in-parallel configurations, a divided wall column uses less energy, capital and space. As the separation is achieved with a single column, it results in significant capital savings. The heavy (C4+) component as a bottom fraction can be routed to an alkylation unit if desired or purged to only recycle partial C4+ heavies back to the metathesis reactor. These and other aspects, embodiments, and features of the processes, methods, facilities, and compositions are described more fully in the Detailed Description and claims and further disclosure such as the Examples provided herein.

DEFINITIONS

Figure 1:
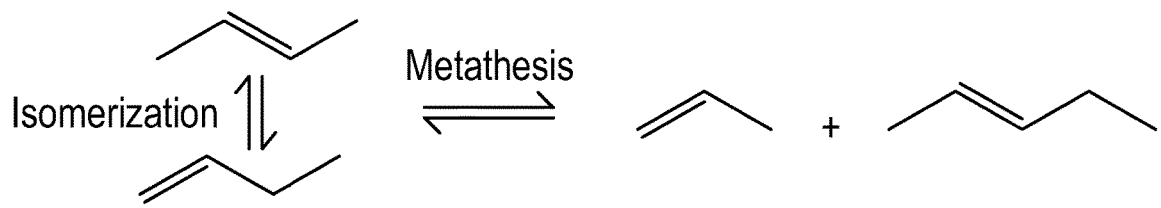
FIG. 1 Illustrates normal butene autometathesis in presence of an isomerization catalyst and a metathesis catalyst.

As used herein, the term "raffinate" or "Raffinate" or "Raff" refers to a residual stream of olefins obtained after the desired chemicals/materials have been removed. In the cracking/crude oil refining process, butene or "C4" raffinate stream refers to the mixed olefin stream recovered from the cracker/fluid catalytic cracking unit. Raffinate 1 refers to the C4 residual olefin stream obtained after separation of butadiene (BD) from the initial C4 Raffinate stream, which provides a mixture rich in 1-butene (B1), 2-butene (B2), and isobutylene (IB). Raffinate 2 refers to the C4 residual olefin stream obtained after separation of both BD and isobutylene (IB) from the initial C4 Raffinate stream, which provides a mixture rich in a mixture of 1-butene (B1) and 2-butene (B2). Therefore, Raffinate 2 can be formed by depleting D3 from Raffinate 1. Raffinate 3 refers to the C4 residual olefin stream obtained after separation of BD, isobutylene, and 1-butene from the initial C4 Raffinate stream, which provides composition rich in 2-butene (B2) (cis- and trans-). Therefore, Raffinate 3 can be formed by depleting B1 from Raffinate 2.

As used herein, the terms "conventional metathesis" and "metathesis" are used interchangeably to refer to the reaction utilizing a C4 hydrocarbon feedstock stream and an ethylene feedstock stream. In contrast, the term "autometathesis" refers to the C4 hydrocarbon feedstock stream undergoing metathesis reactions in the absence of ethylene as a feedstock. Both metathesis and autometathesis reactions may include additional recycle streams containing undesired reaction products that can undergo further reactions with the feedstock stream(s).

The autometathesis methods described herein use a feedstock containing both saturated hydrocarbons and olefins, particularly raffinate streams exiting steam crackers and FCC units. While it is possible to enrich the olefin content by processing the raffinate streams with a diverter to remove saturated hydrocarbons, this is not necessary. The olefin content can also be enriched via known solvent extraction technologies, although again this is not necessary.

As used herein, the term "autometathesis catalyst" refers to the compound or composition that ensures that the autometathesis reaction takes place. The term "isomerization catalyst" is used herein to refer to the compound that is used to rearrange the double bond position in a molecule. Both the autometathesis catalyst and the isomerization catalyst can be used in combination as a metathesis catalyst system in the autometathesis reactor to achieve a synergistic effect.

The autometathesis catalysts used for the methods described herein are W-, Re-, and Mo-based catalyst that are active at low temperatures. Autometathesis catalyst such as $Al_2O_3$ and $SiO_2$ supported $WO_3$ and $MoO_3$ function well, as they have increased selectivity of propylene at the low temperatures used in the presently disclosed methods and are less expensive than Re-based and Ru-based catalysts.

The isomerization catalysts disclosed herein can be Mg- or K-based catalysts, for example, MgO catalyst or $K_2O$ supported on $Al_2O_3$ catalyst.

As used herein, "catalyst support" refers to a material, usually a solid with a high surface area, to which a catalyst is immobilized. The support can be a single inorganic compound or a mixture of inorganic compounds. Exemplary supports can be silica, alumina, zirconia, or zeolite, including γ-aluminum oxide (γ-$Al_2O_3$), aluminum oxide (n-$Al_2O_3$), titanium dioxide ($TiO_2$), zirconium dioxide ($ZrO_2$), silicon dioxide ($SiO_2$), $Al_2O_3$/$SiO_2$, $Al_2O_3$/$B_2O_3$/$SiO_2$, and the like.

A plus sign (+) is used herein to denote a composition of hydrocarbons with the specified number of carbon atoms plus all heavier components. As an example, a C4+ stream comprises hydrocarbons with 4 carbon atoms plus hydrocarbons having 5 or more carbon atoms.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosure.

The following abbreviations are used herein:

| Abbreviation | Term |
|---|---|
| B1 | 1-butene |
| B2 | 2-butenes (including both cis-2-butene and trans-2-butene) |
| IB | isobutylene (i-butylene) |
| NC4 | normal butane (n-butane) |
| IC4 | isobutane (i-butane) |
| BD | butadiene |
| FCC | fluidized catalytic cracker |
| PDH | propane dehydrogenation |
| MTP | methanol to propylene |
| WHSV | weight hourly space velocity |
| VHSV | volume hourly space velocity |
| Raff | raffinate |
| PGP | polymer grade propylene |
| C2= | ethylene |
| C3= | propylene |
| C4= | butenes |
| C5+ | olefins having 5 or more carbons |

Any publications that may be referenced throughout this specification are hereby incorporated by reference in pertinent part in order to more fully describe the state of the art to which the disclosed subject matter pertains. To the extent that any definition or usage provided by any document incorporated herein by reference conflicts with the definition or usage provided in this disclosure, the definition or usage provided in this disclosure controls.

Terms such as "configured for", "adapted for", "adapted to" and similar language is used herein to reflect that the particular recited structure or procedure is used in the recited mixing and separation steps of the disclosed process. For example, unless otherwise specified, a particular structure "configured for use" means it is "configured for use in chemical facility" for the process disclosed herein, therefore is designed, shaped, arranged, constructed, and/or tailored to effect the relevant disclosed mixing and separation steps, as would have been understood by the skilled person.

"Optional" or "optionally" means that the subsequently described event or circumstance can or cannot occur, and that the description includes instances where the event or circumstance occurs and instances where it does not.

Unless indicated otherwise, when a range of any type is disclosed or claimed, for example a range of the percentages, it is intended to disclose or claim individually each possible number that such a range could reasonably encompass, including any sub-ranges or combinations of sub-ranges encompassed therein. When describing a range of measurements such as these, each possible number that such a range could reasonably encompass can, for example, refer to values within the range with one significant figure more than is present in the end points of a range, or refer to values within the range with the same number of significant figures as the end point with the most significant figures, as the context indicates or permits. For example, when describing a range of percentages such as from 85% to 95%, it is understood that this disclosure is intended to encompass each of 85%, 86%, 87%, 88%, 89%, 90%, 91%, 92%, 93%, 94%, and 95%, as well as any ranges, sub-ranges, and combinations of sub-ranges encompassed therein. Applicant's intent is that these two methods of describing the range are interchangeable. Accordingly, Applicant reserves the right to proviso out or exclude any individual members of any such group, including any sub-ranges or combinations of sub-ranges within the group, if for any reason Applicant chooses to claim less than the full measure of the disclosure, for example, to account for a reference that Applicant is unaware of at the time of the filing of the application.

Any headings that are employed herein are not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

Applicants reserve the right to proviso out any selection, feature, range, element, or aspect, for example, to limit the scope of any claim to account for a prior disclosure of which Applicants may be unaware.

DETAILED DESCRIPTION OF THE DISCLOSURE

Aspects of this disclosure provide for a process for upgrading a C4 Raffinate stream to polymer grade propylene (PGP) by a metathesis route, in the absence of using fresh ethylene feedstock. The ethylene byproduct in the metathesis equilibrium may be recycled, which can improve propylene selectivity without adversely affecting butene conversion. Additionally, upon PGP separation, this technology can provide an effluent acceptable for alkylate production. The disclosed process is a relatively low temperature process which can be deployed as a drop-in option in the existing conventional metathesis unit and provide additional flexibility to existing operations to balance the supply and demand of C2-C4 light olefins.

Autometathesis Chemistry. The upgrade of butenes to propylene in C4 Raffinate streams employs olefin metathesis chemistry, specifically, butene autometathesis. Therefore, in aspects of this disclosure, the disclosed olefin metathesis chemistry may be carried out between non-ethylene olefin monomers, in the absence of added (fresh) ethylene. The various butene isomers in the C4 Raffinate feeds can react with each other to yield both propylene and metathesis byproducts, as illustrated in FIG. 1 as an example. The C4 Raffinate feeds comprising 1-butene (B1) and 2-butenes (B2) can equilibrate using an isomerization catalyst such as MgO catalyst or $K_2O$ supported on $Al_2O_3$ catalyst, and this mixture can undergo metathesis in the absence of ethylene as a feedstock to form propylene and 2-pentene as the initial metathesis products. Metathesis catalysts including but not limited to $WO_3$/silica can be used. Further metathesis chemistry can form additional propylene.

As FIG. 1 illustrates, an autometathesis process for a C4 Raffinate feed comprising 1-butene (B1) and 2-butene (B2) in the presence of isomerization catalysts such as MgO or $K_2O/Al_2O_3$ and metathesis catalysts such as $WO_3/SiO_2$ or $MoO_3/Al_2O_3$ can equilibrate butene isomers and undergo metathesis to generate propylene in a process that does not require added ethylene. Metathesis catalysts including but not limited to $WO_3$/silica and/or $MoO_3/Al_2O_3$ can be used, and further metathesis chemistry can form additional propylene. For example, in embodiments, the metathesis catalyst can comprise an oxide of cobalt, molybdenum, rhenium, tungsten, or a combination thereof, supported on a carrier comprising silica, alumina, titania, zirconia, zeolites, clays, or a combination thereof. In another aspect, the metathesis catalyst can comprise $WO_3$, $MoO_3$, or $ReO_3$, or a combination thereof.

An olefin isomerization catalyst can be used in addition to the autometathesis catalyst, which can suppress the formation of heavier hydrocarbons. The olefin isomerization catalyst is also helpful if ethylene is being recycled back into the autometathesis reaction zone. Ethylene reacts with 2-butene to form propylene as in a conventional metathesis unit. An isomerization catalyst which can isomerize 1-butene to 2-butene can promote utilization of the recycled ethylene. The isomerization catalysts are preferably Ca-, Mg-, or K-based catalysts, including basic metal oxides, or mixtures thereof. The isomerization catalyst MgO or $K_2O/Al_2O_3$ can be used.

The processes disclosed herein can utilize relatively low reaction temperatures, and the catalyst's low temperature activity allows the autometathesis reactions to proceed in the liquid phase when using Mo-based catalyst system. In this aspect, the low temperature operation thermodynamically favors production of propylene and reduces coking and results in favorable economic production of propylene. The temperature range for the autometathesis reaction can be between about 70° C. and 300° C. Alternatively, the temperature of the autometathesis reaction can be less than 300° C., between about 150° C. and about 250° C. for W-based catalysts, or between about 70° C. and about 150° C. for Mo-based catalysts.

The pressure range for the autometathesis reaction can be between about 1 bar and about 50 bars pressure. Alternatively, the pressure range can be between about 5 bars and about 30 bars, or between about 20 bars and about 30 bars.

Figure 2:
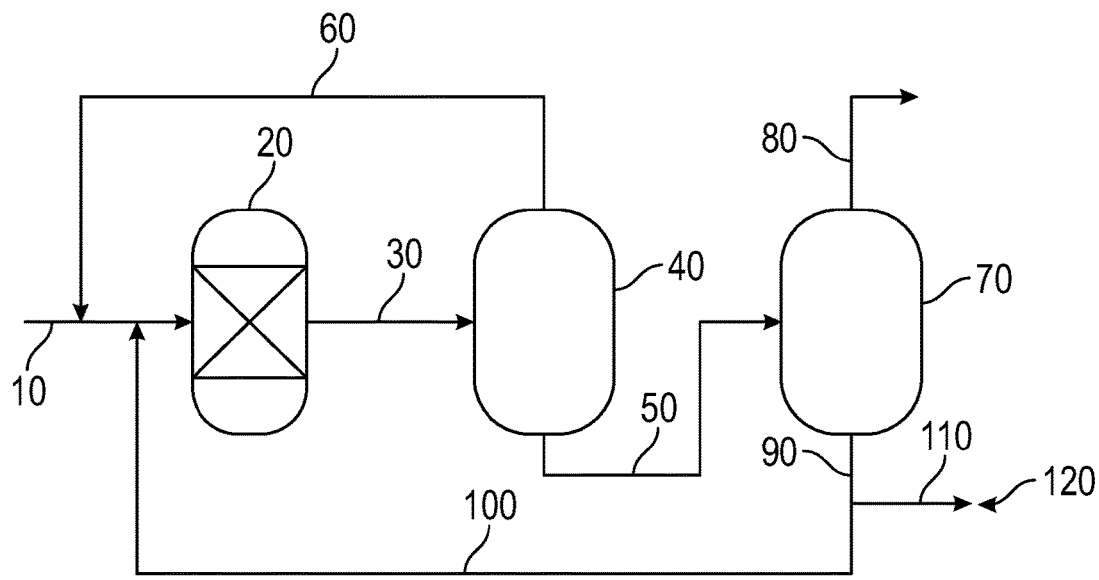
FIG. 2 illustrates an embodiment of the disclosure for converting a C4 Raffinate stream to polymer grade propylene by passing the C4 Raffinate stream through an autometathesis reactor in the absence of ethylene as a feedstock, followed by a de-ethanizer first, followed by passing the C3+ stream through a subsequent de-propanizer.

Process Embodiments. FIG. 2 illustrates certain aspects and embodiments of the disclosure, exemplifying one aspect of the process flow of Raffinate butene to propylene, which utilizes a metathesis reactor followed by a de-ethanizer first, followed by passing the C3+ stream through a subsequent de-propanizer. As shown in FIG. 2, the process for converting a C4 Raffinate stream to propylene can comprise the steps of: a) providing a C4 Raffinate stream 10 comprising 1-butene and 2-butene to a metathesis reactor 20, the metathesis reactor containing a metathesis catalyst system; b) contacting the C4 Raffinate stream 10 with the metathesis catalyst system under conditions suitable for forming an intermediate product stream 30 comprising propylene, a heavy (C4+) component, and ethylene; and c) discharging the intermediate product stream 30 to a first separation unit and separating the intermediate product stream 30 into fractions comprising [1] a first product stream having a higher propylene concentration than the intermediate product stream 30 and [2] a second product stream having a lower propylene concentration than the intermediate product stream 30.

In FIG. 2, the first separation unit which separates the intermediate product stream 30 into a first product stream and a second product stream can comprise a first distillation unit 40 adapted to separate the intermediate product stream 30 into fractions comprising [1] the first product stream 50 comprising propylene and the heavy (C4+) component as a bottom fraction and [2] the second product stream 60 comprising ethylene as an overhead fraction.

Moreover, in embodiments, this process can further comprise recycling the second product stream 60 comprising ethylene to the C4 Raffinate stream 10 or the metathesis reactor 20 of step a) described above. In embodiments, this process may also further comprise the step of discharging the first product stream 50 comprising propylene and the heavy (C4+) component to a second separation unit and separating the first product stream 50 into fractions comprising [1] a third product stream having a higher propylene concentration than the first product stream 50 and [2] a fourth product stream having a lower propylene concentration than the first product stream 50. In this aspect, the second separation unit can comprise a second distillation unit 70 adapted to separate the first product stream 50 into fractions comprising [1] the third product stream 80 comprising propylene as an overhead fraction and [2] the fourth product stream 90 comprising the heavy (C4+) component as the bottom fraction. In embodiments, the second distillation unit 70 may be further adapted to separate the fourth product stream 90 comprising the heavy (C4+) component into fractions comprising [1] a fifth stream 100 comprising C4-C5 components and [2] a purge stream 110 comprising C6+ components. At least a portion of the fifth stream 100 comprising C4-C5 components may be recycled to the C4 Raffinate stream 10 or the metathesis reactor 20 of step a) of the FIG. 2 embodiment if desired. The purge stream 110 comprising C6+ components may be fed to an isomerization reactor containing an isomerization catalyst, wherein at least a portion of the C6+ components undergo an isomerization reaction if desired.

Figure 3:
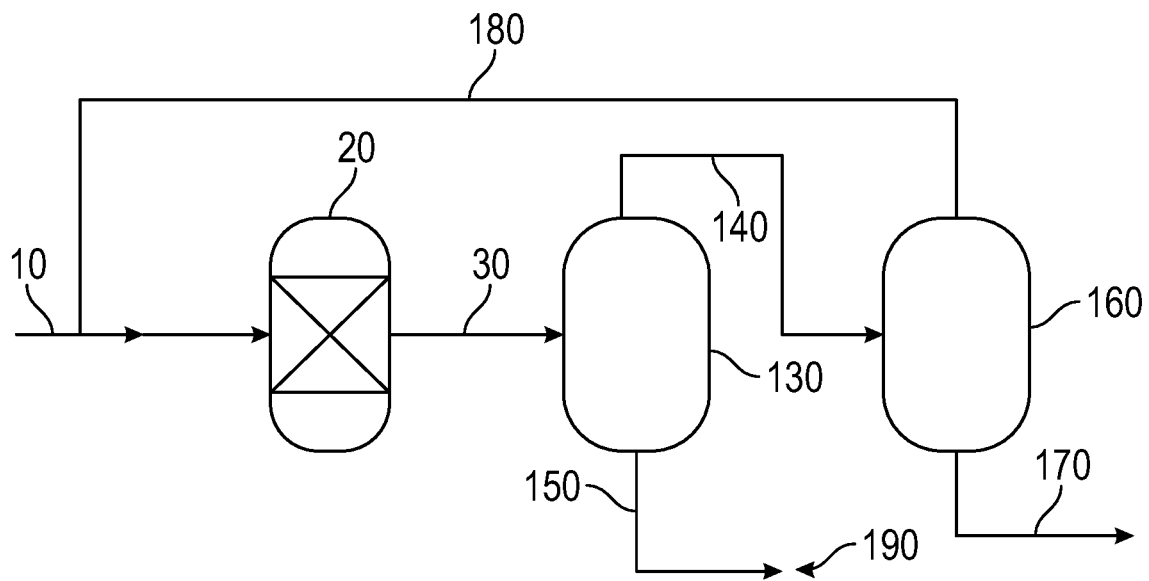
FIG. 3 illustrates an embodiment of the disclosure for converting a C4 Raffinate stream to polymer grade propylene by passing the C4 Raffinate stream through an autometathesis reactor in the absence of ethylene as a feedstock, followed by a de-propanizer first, followed by passing the C2-C3 stream through a subsequent de-ethanizer.

Referring now to FIG. 3, this figure illustrates an embodiment for converting a C4 Raffinate stream to polymer grade propylene by passing the C4 Raffinate stream through a metathesis reactor followed by a de-propanizer first, followed by passing the C2-C3 stream through a subsequent de-ethanizer. The first stage and initial steps of the FIG. 3 embodiment can be the same as the first stage of the FIG. 2 embodiment, namely that of: a) providing a C4 Raffinate stream 10 comprising 1-butene and 2-butene to a metathesis reactor 20, the metathesis reactor containing a metathesis catalyst system; b) contacting the C4 Raffinate stream 10 with the metathesis catalyst under conditions suitable for forming an intermediate product stream 30 comprising propylene, a heavy (C4+) component, and ethylene; and c) discharging the intermediate product stream 30 to a first separation unit and separating the intermediate product stream 30 into fractions comprising [1] a first product stream having a higher propylene concentration than the intermediate product stream 30 and [2] a second product stream having a lower propylene concentration than the intermediate product stream 30.

In the FIG. 3 embodiment, the first separation unit can comprise a first distillation unit 130 adapted to separate the intermediate product stream 30 into [1] the first product stream 140 comprising propylene and ethylene as an overhead fraction and [2] the second product stream 150 comprising the heavy (C4+) component as a bottom fraction. The first product stream 140 comprising propylene and ethylene can then be discharged to a second separation unit and separating the first product stream 140 into [1] a third product stream having a higher propylene concentration than the first product stream 140 and [2] a fourth product stream having a lower propylene concentration than the first product stream 140. In this aspect, the second separation unit can comprise a second distillation unit 160 adapted to separate the first product stream 140 into [1] the third product stream 170 comprising propylene as a bottom fraction and [2] the fourth product stream 180 comprising ethylene as an overhead fraction. If desired, the fourth product stream 180 comprising ethylene can be recycled to the C4 Raffinate stream 10 of step a) in the FIG. 3 description. Moreover, the second product stream 150 comprising the heavy (C4+) component may be fed to an alkylation reactor 190 comprising an alkylation catalyst, wherein at least a portion of the heavy (C4+) component undergoes an alkylation reaction.

Figure 4:
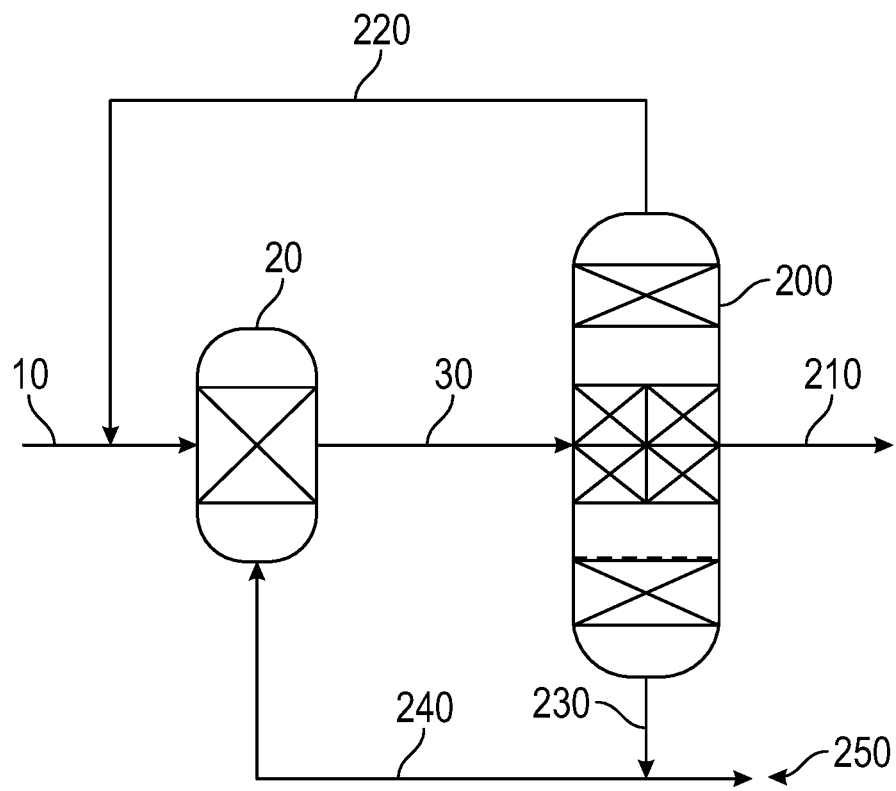
FIG. 4 illustrates an embodiment of the disclosure for converting a C4 Raffinate stream to polymer grade propylene by passing the C4 Raffinate stream through an autometathesis reactor followed by a divided wall column.

FIG. 4 illustrates yet another embodiment for a process for converting a C4 Raffinate stream to polymer grade propylene by passing the C4 Raffinate stream through a metathesis reactor followed by a divided wall column, which can separate the intermediate product stream into various fractions. As in the FIG. 2 and FIG. 3 embodiments, the first stage and initial steps of the FIG. 4 embodiment can be the same as the first stage of the FIG. 2 and FIG. 3 embodiments, namely: a) providing a C4 Raffinate stream 10 comprising 1-butene and 2-butene to a metathesis reactor 20, the metathesis reactor containing a metathesis catalyst; b) contacting the C4 Raffinate stream 10 with the metathesis catalyst system under conditions suitable for forming an intermediate product stream 30 comprising propylene, a heavy (C4+) component, and ethylene; and c) discharging the intermediate product stream 30 to a first separation unit and separating the intermediate product stream 30 into fractions comprising [1] a first product stream having a higher propylene concentration than the intermediate product stream 30 and [2] a second product stream having a lower propylene concentration than the intermediate product stream 30.

In this FIG. 4 embodiment, the first separation unit can comprise a divided wall distillation unit 200 adapted to separate the intermediate product stream 30 into fractions comprising [1] the first product stream 210 comprising propylene as a side fraction, [2] the second product stream 220 comprising ethylene as an overhead fraction, and [3] a third product stream 230 comprising the heavy (C4+) component as a bottom fraction. The second product stream 220 comprising ethylene may be recycled to the C4 Raffinate stream 10 or the metathesis reactor 20 of step a) described above. The third product stream 230 can be separated into a heavy (C4+) component stream 240, at least a portion of which can be recycled to the C4 Raffinate stream 10 or to the metathesis reactor 20 of step a), and a purge stream 250 comprising C6+ components.

Not illustrated in FIG. 4 is the feature that additional side streams may be provided using a divided wall column. For example, the first separation unit can comprise a divided wall distillation unit 200 adapted to separate the intermediate product stream 30 into fractions comprising [1] the first product stream comprising propylene as a first side fraction, [2] the second product stream comprising ethylene as an overhead fraction, [3] a third product stream comprising a C4 component as a bottom fraction, and [4] a fourth product stream comprising a C5+ component as a second side fraction. In this aspect, the second product stream comprising ethylene may be recycled to the C4 Raffinate stream 10 or the metathesis reactor 20 of step a) described above. Also in this aspect, the at least a portion of the third product stream comprising a C4 component may be recycled to the C4 Raffinate stream 10 or to the metathesis reactor 20 of step a) described above.

In each of the aspects and embodiments described above, the C4 Raffinate stream is contacted with the metathesis catalyst system in the absence of ethylene as a feedstock. Ethylene which is generated in subsequent separation processes can be recycled to the C4 Raffinate feed stream or directly to the metathesis reactor, but no fresh ethylene is needed for these processes to operate.

In each embodiment described herein, prior to the C4 Raffinate stream contacting the metathesis catalyst system in the metathesis reactor, the C4 Raffinate stream can undergo a treatment that can clean the C4 Raffinate feed from trace contaminants. For example, the C4 Raffinate feed can be passed through a 13× molecular sieve treatment stage located upstream of the metathesis reactor to clean the feed from trace contaminants such as oxygenates. Other treatment or pretreatment stages can be used as needed or desired to target and remove various contaminants.

Feeds. Suitable feeds for the propylene production according to this disclosure include, but are not limited to, raffinate products obtained from the extractive distillation of the crude C4 product from an olefins plant in which the diolefins such as 1,4-butadiene have been preferentially removed. This raffinate product, which may be termed Raffinate 1, is rich in a mixture of 1-butene (B1), 2-butene (B2), and isobutylene (i-butylene), which are useful in the disclosed process. A Raffinate 1 stream may be further depleted of isobutylene to afford a product termed Raffinate 2, which rich in a mixture of 1-butene (B1) and 2-butene (B2). A Raffinate 2 stream may itself be depleted of 1-butene (B1) to form a Raffinate 3 (or Raffinate-3) which is rich in 2-butene (B2) (cis- and trans-). Raffinate 1, Raffinate 2 and Raffinate 3 are useful in the disclosed process, and combinations of any of Raffinate 1, Raffinate 2, and Raffinate 3 are useful in the disclosed process. Particularly the metathesis process may be combined with an olefin isomerization process which can interconvert B1 and B2 using, for example, a MgO catalyst or $K_2O/Al_2O_3$.

Accordingly, the C4 Raffinate stream 10 can comprises a Raffinate 1, a Raffinate 2, a Raffinate 3, or a combination thereof, from a steam cracker unit or a fluidized catalytic cracker unit. In an aspect, this process C4 Raffinate (C4 Raffinate) stream may be upgraded to propylene which can produce polymer grade propylene (PGP) by a metathesis process, without consuming fresh ethylene. Therefore, in any of the disclosed embodiments, the C4 Raffinate stream 10 which comprises 1-butene and 2-butene and is provided to a metathesis reactor, can be absent any added ethylene, that is, absent ethylene as a feedstock such that no ethylene other than that occurring in the C4 Raffinate stream is added to the C4 Raffinate stream or directly to the metathesis reactor. Therefore, step b) of the process of contacting the C4 Raffinate stream 10 with the metathesis catalyst may occur in the absence of any ethylene as a feedstock.

EXAMPLES

Materials and Procedures. Experiments were performed with a high pressure olefin unit using a fixed bed reactor.

TABLE 1

C4 Raffinate feed specifications

| Chemical | Description |
| --- | --- |
| B1/B2 only | B1/B2 of 50/50 |
| Raffinate 2 | 22% B2, 21% NC4, 26% IC4, 4% IB, and 27% B1 |
| Raffinate 1 | 21% B1, 11% B2, 12% NC4, 17% IC4, 39% IB |

Abbreviations:
B1, 1-butene;
B2, 2-butene;
NC4, n-butane;
IC4, isobutane;
IB, isobutylene Process Conditions Process steps in a typical experiment were: 1) loading a specific amount of catalysts; 2) installing the reactor on the process; 3) activating the catalyst at 475° C. with argon flow under ambient pressure; 4) cooling the reactor down to the process temperature with continued argon flow; 5) blocking the argon and setting up the back-pressure regulator to 450 psig; 6) feeding hydrocarbons of desired WHSVs (weight hourly space velocities, /h) and monitoring the effluent using online GC (gas chromatography) before the thermal oxidizer (TO); 7) venting off the residual hydrocarbons after a desired time on stream to the TO and returning the reactor pressure/temperature to ambient with house argon purging; and 8) taking the reactor off the process line or regenerating the catalyst with house nitrogen/air.

This Raffinate butene to propylene process can serve as a drop-in operation for an existing conventional metathesis unit to offer an additional process flexibility.

Example 1

Butene Autometathesis with Various Metathesis Catalyst System

Experimental results have shown that MgO and $WO_3$ catalyst system can achieve a thermodynamic equilibrium at a significant lower temperature than previously thought absent an equal molar amount of fresh ethylene co-feed. Furthermore, it is found that the presence of MgO suppresses C5 and heavies coproduction though slightly reducing the C4 conversion, Table 2. Because the Raffinate butenes to propylene process is considered to integrate with the alkylation operation, the decreased C4 conversion actually increases the effluent C4/C5 ratio, making it more acceptable for the alkylation operation without adversely affecting the final alkylate quality, that is, octane number and D86 end point (EP). Significant heavies olefins (C5+) in the alkylation feeds is undesirable for final alkylate quality as it lowers the octane number and raises D86 EP.

TABLE 2

Experimental results at 200° C., 450 psig and various catalyst loadings (B1 is 1-butene).

| Catalyst | B1/total B(%) | C2= selectivity (mol %) | C3= selectivity (mol %) | C5+ selectivity (mol %) | C4= conversion (wt %) |
|---|---|---|---|---|---|
| $WO_3$ | 30.81 | 3.77 | 34.73 | 61.51 | 66.66 |
| $MgO/WO_3$ = (1:1) | 12.72 | 4.47 | 51.40 | 44.13 | 54.97 |
| $MgO(WO_3/MgO)$ = 1:(1:3) | 11.41 | 4.42 | 50.92 | 44.66 | 54.93 |

Figure 5:
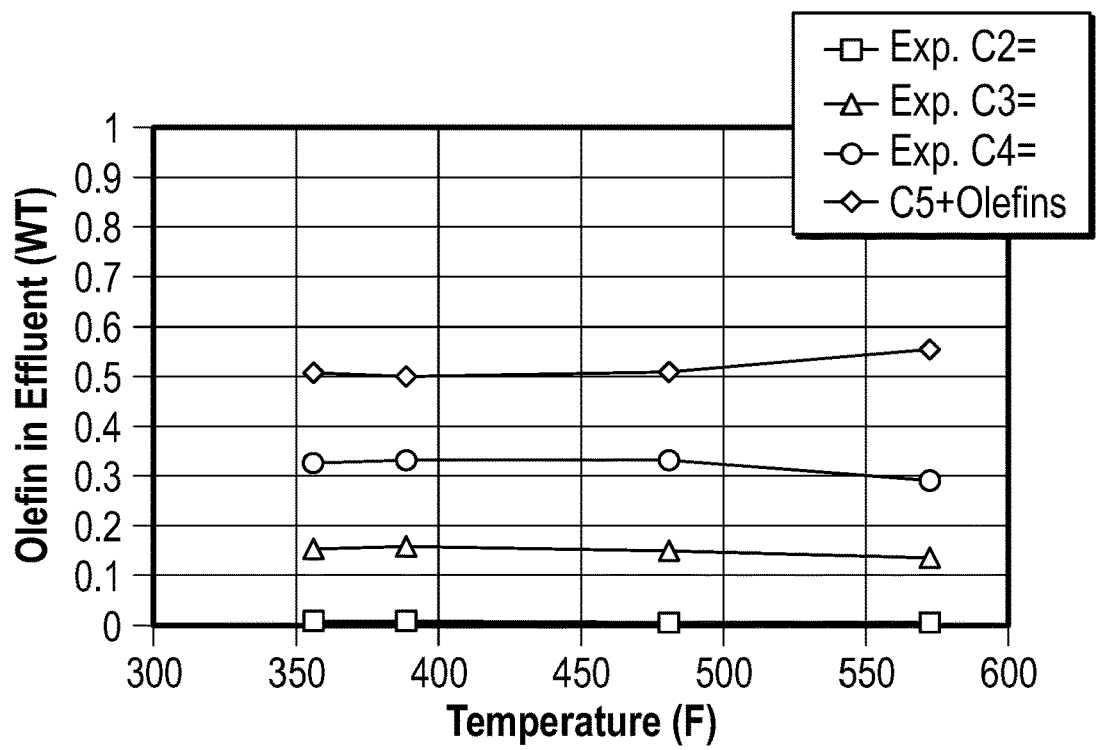
FIG. 5 illustrates the experimental olefin distribution in the effluent for butene autometathesis of a feed having a 50/50 1-butene (B1)/2-butene (B2) mixture using a autometathesis catalyst only, with no isomerization catalyst present, as in Example 1.

Without an isomerization catalyst present, the product distribution was heavily dependent on the B1/B2 composition in the feed. For Raffinate 2, typically having B1/B2 of 50/50 after MTBE process, results from experiments with the metathesis catalyst $WO_3$ only show relatively high Flex gasoline production and butene conversion and relatively low propylene yield. See FIG. 5. Because heavier olefins are less attractive than butenes as an alkylation olefin feed, catalyst loadings that included the presence of both an isomerization catalyst and a metathesis catalysts were useful to suppress the heavies formation, while promoting propylene selectivity and production.

Example 2

Butene Autometathesis with Both Isomerization/Metathesis Catalyst

Figure 6:
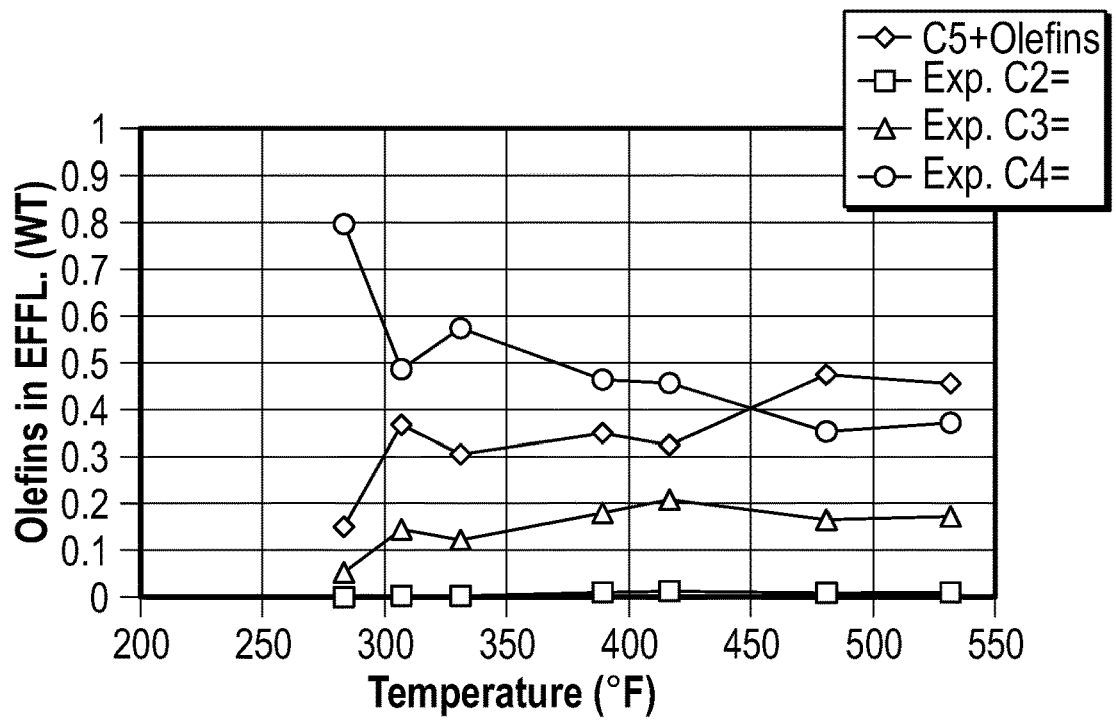
FIG. 6 illustrates a plot of the experimental olefin distribution in the effluent for Raffinate butene autometathesis using an isomerization catalyst and autometathesis catalyst MgO/$WO_3$ in a 1:1 mass ratio, according to Example 2.

In the presence of an isomerization catalyst, for example a metathesis catalyst loading consisting of $MgO/WO_3$ at 1:1 mass ratio, a product distribution in FIG. 6 was achieved. A process temperature of 390±10° F. was exhibited as the preferred process temperature, because reactions were able to reach equilibrium and achieve a balanced propylene yield versus butene conversion for subsequent alkylation process at this temperature. Temperatures higher than 390±10° F. lead to increased heavy byproducts while the process displayed a kinetic limitation at lower temperatures.

Example 3

Ethylene Recycle

It was surprisingly discovered that the $MgO/WO_3$/silica metathesis catalyst system has the ability to reach equilibrium for butene autometathesis at lower temperature, for example 200° C., without the presence of significant ethylene, such as when no fresh ethylene is added in the metathesis reaction. The conventional on purpose metathesis for propylene from ethylene/butene with W-catalyst system can use temperatures of at least 250° C. to reach thermodynamic equilibrium.

Figure 7:
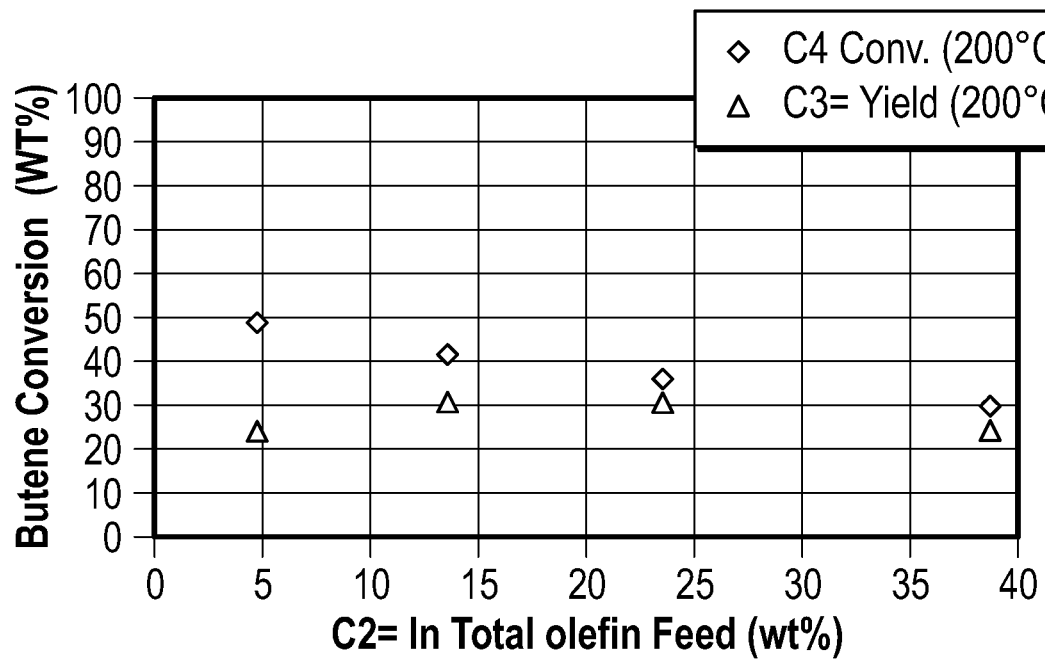
FIG. 7 provides a plot of the experimental results of the impact of ethylene on butene conversion and propylene yield at 200° C.

As demonstrated in the various embodiments of this process, the raffinate butene to propylene conversion by a metathesis process can be effected without consuming fresh ethylene. However, ethylene byproduct from the metathesis can be recycled into the butene raffinate stream or the metathesis reactor. When ethylene is recycled in this manner, it has been found that ethylene should be present at a concentration of not more than about 15 wt % of the feed at 200° C. for MgO and $WO_3$/Silica metathesis catalyst system. It has been observed that ethylene concentrations in excess of about 15 wt % reduce the catalyst activity thereby preventing the process from reaching equilibrium, as illustrated in FIG. 7. The ethylene molecule is smaller and therefore is thought to compete efficiently against butenes to coordinate active catalyst sites and participate in the metathesis process. At temperatures lower than about 200° C., the coordination of ethylene is sufficiently strong as to limit butene access, thereby raising the activation barrier for butene conversion and resulting in a lower propylene yield. In such situations, the propylene yield and butene conversion cannot reach equilibrium and become kinetically limited with MgO and $WO_3$/silica metathesis catalyst system.

Example 4

Process Throughput

A wide range of process flows, WHSVs (weight hourly space velocities, /h) from 1 to 8.3/h, were investigated for the disclosed butene autometathesis to propylene process at lower process temperature. Results have showed that the process can reach equilibrium under all investigated throughput conditions. The ability to achieve equilibria under high throughputs is a desirable feature for commercial implementation as it provides maximal benefit to debottleneck and upgrade.

Example 5

Catalyst Life on Stream

Figure 8:
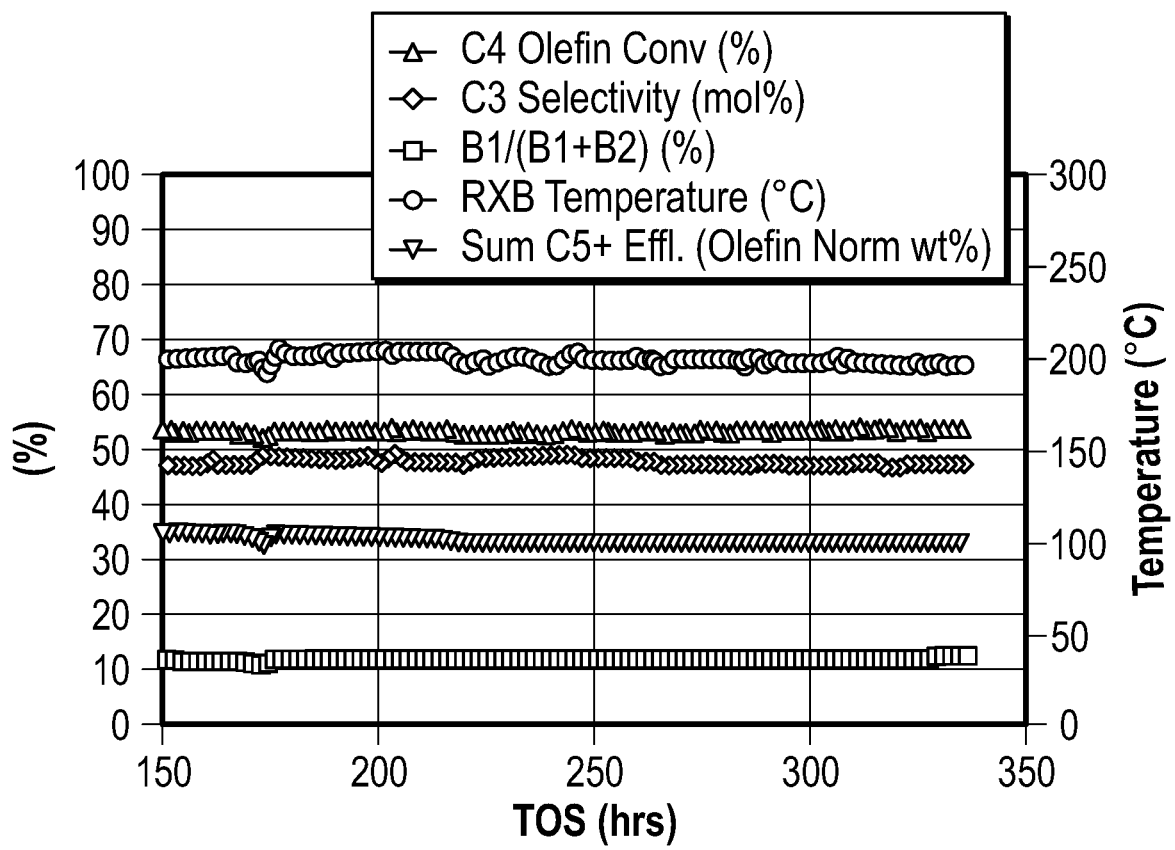
FIG. 8 provides the process result over time of a Raffinate butene feed to propylene conversion using MgO/$WO_3$ at 200° C. and 450 psig.

Another benefit of lower process temperature is the extended run length due to the reduced coking rate under mild process condition as demonstrated in FIG. 8

The following references are incorporated by reference in their entireties: U.S. Pat. Nos. 6,580,009; 6,646,172;

US20170001927; U.S. Pat. Nos. 8,722,950; 9,422,209; 6,777,582; and 8,704,029. These and other aspects of the disclosure are provided in the appended claims.

We claim:

1. A process for converting a C4 Raffinate stream to propylene, the process comprising:
    a) providing a C4 Raffinate stream comprising 1-butene and 2-butene to a metathesis reactor, the metathesis reactor containing a metathesis catalyst system, wherein the C4 Raffinate stream is provided as a weight hourly space velocity ranging from 1 to 8.3/h;
    b) contacting the C4 Raffinate stream with the metathesis catalyst system under conditions suitable for forming an intermediate product stream comprising propylene, a heavy (C4+) component, and ethylene; and
    c) discharging the intermediate product stream to a first separation unit and separating the intermediate product stream into fractions comprising [1] a first product stream having a higher propylene concentration than the intermediate product stream and [2] a second product stream having a lower propylene concentration than the intermediate product stream, wherein the second product stream contains ethylene but in an amount less than 15 wt. %, wherein the second product stream is recycled by combining the second product stream with the C4 Raffinate stream or is recycled by introduction into the metathesis reactor, and
wherein the process for converting the C4 Raffinate stream to propylene is performed in the absence of added ethylene.

2. The process according to claim 1, wherein the first separation unit comprises a first distillation unit adapted to separate the intermediate product stream into fractions comprising [1] the first product stream comprising propylene and the heavy (C4+) component as a bottom fraction.

3. The process according to claim 2, wherein the second product stream comprising ethylene is recycled, as a recycled source of ethylene, to the C4 Raffinate stream.

4. The process according to claim 2, wherein the first product stream comprising propylene and the heavy (C4+) component is discharged to a second separation unit and separating the first product stream into fractions comprising [1] a third product stream having a higher propylene concentration than the first product stream and [2] a fourth product stream having a lower propylene concentration than the first product stream.

5. The process according to claim 4, wherein the second separation unit comprises a second distillation unit adapted to separate the first product stream into fractions comprising [1] the third product stream comprising propylene as an overhead fraction and [2] the fourth product stream comprising the heavy (C4+) component as the bottom fraction.

6. The process according to claim 5, wherein the second distillation unit is further adapted to separate the fourth product stream comprising the heavy (C4+) component into fractions comprising [1] a fifth stream comprising C4-C5 components and [2] a purge stream comprising C6+ components.

7. The process according to claim 6, wherein at least a portion of the fifth stream comprising C4-C5 components is recycled to the C4 Raffinate stream or the metathesis reactor of step a).

8. The process according to claim 6, wherein the purge stream comprising C6+ components is fed to an isomerization reactor containing an isomerization catalyst, wherein at least a portion of the C6+ components undergo an isomerization reaction.

9. The process according to claim 1, wherein the first separation unit comprises a first distillation unit adapted to separate the intermediate product stream into [1] the first product stream as a bottom fraction and [2] the second product stream as an overhead fraction.

10. The process according to claim 9, wherein the second product stream comprising propylene and ethylene is discharged to a second separation unit and separating the second product stream into [1] a third product stream having a higher propylene concentration than the second product stream and [2] a fourth product stream having a lower propylene concentration than the second product stream.

11. The process according to claim 10, wherein the second separation unit comprises a second distillation unit adapted to separate the second product stream into [1] the third product stream comprising propylene as a bottom fraction and [2] the fourth product stream comprising ethylene as an overhead fraction.

12. The process according to claim 9, wherein the first product stream comprising the heavy (C4+) component is fed to an alkylation reactor.

13. The process according to claim 1, wherein the first separation unit comprises a divided wall distillation unit adapted to separate the intermediate product stream into fractions comprising [1] the first product stream comprising propylene as a side fraction, [2] the second product stream comprising ethylene as an overhead fraction, and [3] a third product stream comprising the heavy (C4+) component as a bottom fraction.

14. The process according to claim 13, wherein at least a portion of the third product stream comprising the heavy (C4+) component is recycled to the C4 Raffinate stream or to the metathesis reactor of step a).

15. The process according to claim 1, wherein the first separation unit comprises a divided wall distillation unit adapted to separate the intermediate product stream into fractions comprising [1] the first product stream comprising propylene as a first side fraction,
[2] the second product stream comprising ethylene as an overhead fraction, [3] a third product stream comprising a C4 component as a bottom fraction, and [4] a fourth product stream comprising a C5+ component as a second side fraction.

16. The process according to claim 15, wherein:
    d) the second product stream comprising ethylene is recycled to the C4 Raffinate stream or the metathesis reactor of step a); and
    e) at least a portion of the third product stream comprising a C4 component is recycled to the C4 Raffinate stream or to the metathesis reactor of step a).

17. The process according to claim 1, wherein the metathesis catalyst system comprises an oxide of cobalt, molybdenum, rhenium, tungsten, or a combination thereof, supported on a carrier comprising silica, alumina, titania, zirconia, zeolites, clays, or a combination thereof.

18. The process according to claim 1, wherein step b) of contacting the C4 Raffinate stream with the metathesis catalyst system further comprises contacting the C4 Raffinate stream with an isomerization catalyst.

* * * * *